United States Patent
Lee et al.

(10) Patent No.: US 11,214,532 B2
(45) Date of Patent: Jan. 4, 2022

(54) PREPARATION METHOD FOR CYCLOHEXANE DIMETHANOL HAVING HIGH TRANS CONTENT AND CYCLOHEXANE DIMETHANOL PREPARED THEREBY

(71) Applicant: HANWHA SOLUTIONS CORPORATION, Seoul (KR)

(72) Inventors: Jong Kwon Lee, Daejeon (KR); Ki Don Kim, Seoul (KR); Eun Jeong Kim, Daejeon (KR); Joo Hee Han, Yongin-si (KR); Ho Seong Nam, Daejeon (KR)

(73) Assignee: HANWHA SOLUTIONS CORPORATION, Seoul (KR)

( * ) Notice: Subject to any disclaimer, the term of this patent is extended or adjusted under 35 U.S.C. 154(b) by 0 days.

(21) Appl. No.: 16/955,421

(22) PCT Filed: Dec. 21, 2018

(86) PCT No.: PCT/KR2018/016516
§ 371 (c)(1),
(2) Date: Jun. 18, 2020

(87) PCT Pub. No.: WO2019/125071
PCT Pub. Date: Jun. 27, 2019

(65) Prior Publication Data
US 2021/0070682 A1   Mar. 11, 2021

(30) Foreign Application Priority Data
Dec. 22, 2017   (KR) .......................... 10-2017-0178151

(51) Int. Cl.
| | | |
|---|---|---|
| *C07C 29/147* | (2006.01) | |
| *C07C 29/149* | (2006.01) | |
| *C07C 31/27* | (2006.01) | |
| *C07C 29/56* | (2006.01) | |
| *B01J 21/04* | (2006.01) | |
| *B01J 23/46* | (2006.01) | |
| *B01J 23/755* | (2006.01) | |
| *B01J 23/44* | (2006.01) | |
| *B01J 23/40* | (2006.01) | |
| *B01J 23/42* | (2006.01) | |
| *B01J 23/14* | (2006.01) | |
| *B01J 21/06* | (2006.01) | |
| *B01J 21/10* | (2006.01) | |
| *B01J 21/08* | (2006.01) | |

(52) U.S. Cl.
CPC .............. *C07C 31/276* (2013.01); *B01J 21/04* (2013.01); *B01J 21/06* (2013.01); *B01J 21/063* (2013.01); *B01J 21/066* (2013.01); *B01J 21/10* (2013.01); *B01J 23/14* (2013.01); *B01J 23/40* (2013.01); *B01J 23/42* (2013.01); *B01J 23/44* (2013.01); *B01J 23/462* (2013.01); *B01J 23/464* (2013.01); *B01J 23/755* (2013.01); *C07C 29/147* (2013.01); *C07C 29/149* (2013.01); *B01J 21/08* (2013.01); *B01J 2523/3712* (2013.01); *C07C 2601/14* (2017.05)

(58) Field of Classification Search
None
See application file for complete search history.

(56) References Cited

U.S. PATENT DOCUMENTS

| | | | |
|---|---|---|---|
| 5,395,986 A | 3/1995 | Scarlett et al. | |
| 5,395,987 A | 3/1995 | Rathmell et al. | |
| 6,294,703 B1 | 9/2001 | Hara et al. | |
| 6,455,664 B1 * | 9/2002 | Patel | C08G 63/199 528/272 |
| 6,495,730 B1 | 12/2002 | Konishi et al. | |
| 9,663,426 B2 | 5/2017 | Choi et al. | |
| 2015/0183706 A1 | 7/2015 | Hembre et al. | |
| 2017/0107164 A1 | 4/2017 | Choi et al. | |
| 2019/0202761 A1 * | 7/2019 | Cha | B01J 35/1066 |

FOREIGN PATENT DOCUMENTS

| | | | |
|---|---|---|---|
| CN | 1915958 A | | 2/2007 |
| CN | 105582927 A | * | 5/2016 |
| CN | 107282045 A | * | 10/2017 |
| JP | 2000-80053 A | | 3/2000 |
| JP | 2002363126 A | * | 12/2002 |
| JP | 2014-177422 A | | 9/2014 |
| KR | 10-2016-0056208 A | | 5/2016 |
| WO | 2015/178459 A1 | | 11/2015 |

OTHER PUBLICATIONS

CN107282045A, English translation, Oct. 2017 (Year: 2017).*
CN105582927A, English translation, May 2016 (Year: 2016).*
Song, S. et al. "Robust cobalt oxide catalysts for controllable hydrogenation of carboxylic acids to alcohols" Chinese Journal of Catalysis 39 (2018) 250-257; Published Feb. 5, 2018 (Year: 2018).*
ChemIDplus (1,4-cyclohexanedimethanol; Deposited Mar. 21, 2012) (Year: 2012).*
JP-2002363126-A, English translation, Dec. 18, 2002 (Year: 2002).*
International Search Report dated Apr. 5, 2019 in International Application No. PCT/KR2018/016516.

* cited by examiner

*Primary Examiner* — Medhanit W Bahta
(74) *Attorney, Agent, or Firm* — Sughrue Mion, PLLC

(57) ABSTRACT

Provided is a preparation method for a cyclohexane dimethanol (CHDM), which can have a high trans content through particular conditions, additive addition, or reactant addition, which is controlled in a cyclohexane dicarboxylic acid (CHDA) hydrogenation reaction, and a cyclohexane dimethanol prepared thereby.

10 Claims, 7 Drawing Sheets

PREPARATION METHOD FOR CYCLOHEXANE DIMETHANOL HAVING HIGH TRANS CONTENT AND CYCLOHEXANE DIMETHANOL PREPARED THEREBY

CROSS REFERENCE TO RELATED APPLICATIONS

This application is a National Stage of International Application No. PCT/KR2018/016516, filed Dec. 21, 2018, claiming priority to Korean Patent Application No. 10-2017-0178151, filed Dec. 22, 2017.

TECHNICAL FIELD

The present invention relates to a preparation method for a cyclohexane dimethanol (CHDM) having a high trans content and a cyclohexane dimethanol prepared thereby, and more particularly, to a preparation method for a cyclohexane dimethanol, which can have a high trans content through particular conditions, additive addition, or reactant addition, which is controlled in a cyclohexane dicarboxylic acid (CHDA) hydrogenation reaction, and a cyclohexane dimethanol prepared thereby.

BACKGROUND ART

Cyclohexane dimethanol (CHDM, 1,4-cyclohexanedimethanol) is the basic raw material for the preparation of polyester or polyamide resins. CHDM is commercially prepared in Asia by SK NJC, which is a joint-venture firm established by SK Chemicals, Mitsubishi Corporation, and Shin Nippon Rika. Indorama [old name: Eastman] is dominating the entire markets all over the world. In the CHDM market, a demand for high value-added polyester resins is increasing and is expected to increase in the future. Thus, stable supply and demand is required. Currently, Indorama produces 100 KTA of CHDM and SK NJC produces 20 KTA of CHDM. It is known that SK NJC plans to increase the production to 60 KTA by 2018. It is known that one production line has recently been expanded in two existing production lines.

According to the known documents, there are three methods for preparing a CHDM using a purified terephthalic acid (PTA). According to a first method, salt is produced by ionizing PTA of Sumitomo Seika Chemicals Co., Ltd. with NaOH in an aqueous solution to increase PTA solubility and a hydrogenation reaction is performed. This synthesis method has an advantage that lowers a hydrogenation reaction temperature as PTA solubility increases at a low temperature (40° C. to 130° C.). However, after the reaction, a process of neutralizing with HCl to recover $Na^+$ ions is required. After the residual $Na^+$ salt reacts, it affects PETG polymerization. Also, a brine solution containing NaCl incurs excessive wastewater treatment costs. This adversely affects the cost reduction of the production process. A second method is a preparation method used by Indorama and SK NJC. Dimethyl terephthalate (DMT) is prepared by esterifying PTA and CHDM is prepared through dimethyl cyclohexane dicarboxylate (DMCD). Since this process uses a Cu-based or Cr-based catalyst when preparing CHDM from DMCD, it is relatively inexpensive in terms of catalyst price. However, since this process is a three-step preparation process (PTA→DMT→DMCD→CHDM), it is disadvantageous in terms of process. On the other hand, a third method is a process of preparing CHDM from PTA through CHDA.

Since ruthenium, which is a noble metal, is used as an active metal in a CHDA hydrogenation reaction, it is disadvantageous in terms of catalyst price. However, since the final product CHDM can be obtained through the two-step process (PTA→CHDA→CHDM), it is determined that this process is advantageous in terms of cost reduction if the product cost is reduced through a reduction in process steps and the competitiveness of process technology is secured.

However, a method of obtaining a CHDM having a high trans content even in the case of preparing a CHDM using such a conventional CHDA hydrogenation reaction has not been disclosed, and a demand for such a method is still required.

DESCRIPTION OF EMBODIMENTS

Technical Problem

The present invention aims to solve the above-described problems of the related art and the technical problems requested from the past.

An object of the present invention is to provide a preparation method for a cyclohexane dimethanol having a high trans content so as to increase heat resistance of a crystalline polymer, when used as a polymerization raw material, wherein the preparation method uses reaction conditions, additive, or reactants having a variety of trans content in a hydrogenation reaction of a cyclohexane dicarboxylic acid (CHDA), and a cyclohexane dimethanol prepared thereby.

Solution to Problem

In order to achieve the objects, the present invention provides a method for preparing a cyclohexane dimethanol (CHDM).

The cyclohexane dimethanol (CHDM) is prepared by performing a hydrogenation reaction of a catalyst and a cyclohexane dicarboxylic acid (CHDA), wherein a weight ratio of the catalyst to the cyclohexane dicarboxylic acid (CHDA) is 1:1 to 1:5.

In one preferred embodiment of the present invention, at least one selected from a homogeneous additive and a heterogeneous additive may be further included in the hydrogenation reaction.

In one preferred embodiment of the present invention, the homogeneous additive may include at least one selected from the group consisting of ammonium bicarbonate ($NH_4HCO_3$), sodium hydroxide (NaOH), potassium carbonate ($K_2CO_3$), and sodium borohydride ($NaBH_4$), and the heterogeneous additive may include at least one selected from the group consisting of zirconia, titania, ceria, silica, and magnesia.

In one preferred embodiment of the present invention, a weight ratio of the homogeneous additive to the catalyst may be 1:0.05 to 1:1.

In one preferred embodiment of the present invention, a weight ratio of the heterogeneous additive to the catalyst may be 1:0.5 to 1:3.

In one preferred embodiment of the present invention, the hydrogenation reaction of the cyclohexane dicarboxylic acid (CHDA) may be performed in a temperature range of 200° C. to 280° C.

In one preferred embodiment of the present invention, the hydrogenation reaction of the cyclohexane dicarboxylic acid (CHDA) may be performed in a pressure range of 50 bar to 150 bar.

In one preferred embodiment of the present invention, the hydrogenation reaction of the cyclohexane dicarboxylic acid (CHDA) may be performed for 1 hour to 8 hours.

In one preferred embodiment of the present invention, the cyclohexane dicarboxylic acid (CHDA) may use a reactant selected from a cis form, a trans form, and a mixed form thereof.

In one preferred embodiment of the present invention, the cyclohexane dimethanol (CHDM) may have a yield of 85% to 99%.

In one preferred embodiment of the present invention, the catalyst may include at least one selected from the group consisting of ruthenium (Ru), palladium (Pd), rhodium (Rh), platinum (Pt), tin (Sn), and nickel (Ni).

In one preferred embodiment of the present invention, the method may include an isomerization reaction process of the cyclohexane dicarboxylic acid (CHDA).

The present invention provides a cyclohexane dimethanol (CHDM) prepared by the above-described method.

In one preferred embodiment of the present invention, a trans ratio of the cyclohexane dimethanol (CHDM) may be within a range of 60% to 95%.

Advantageous Effects of Disclosure

As described above, the present invention has an effect that can obtain a cyclohexane dimethanol having a high trans content so as to increase heat resistance of a crystalline polymer, when used as a polymerization raw material, through a preparation method using reaction conditions, additive, or reactants having a variety of trans content in a hydrogenation reaction of a cyclohexane dicarboxylic acid (CHDA).

BEST MODE

Figure 1:
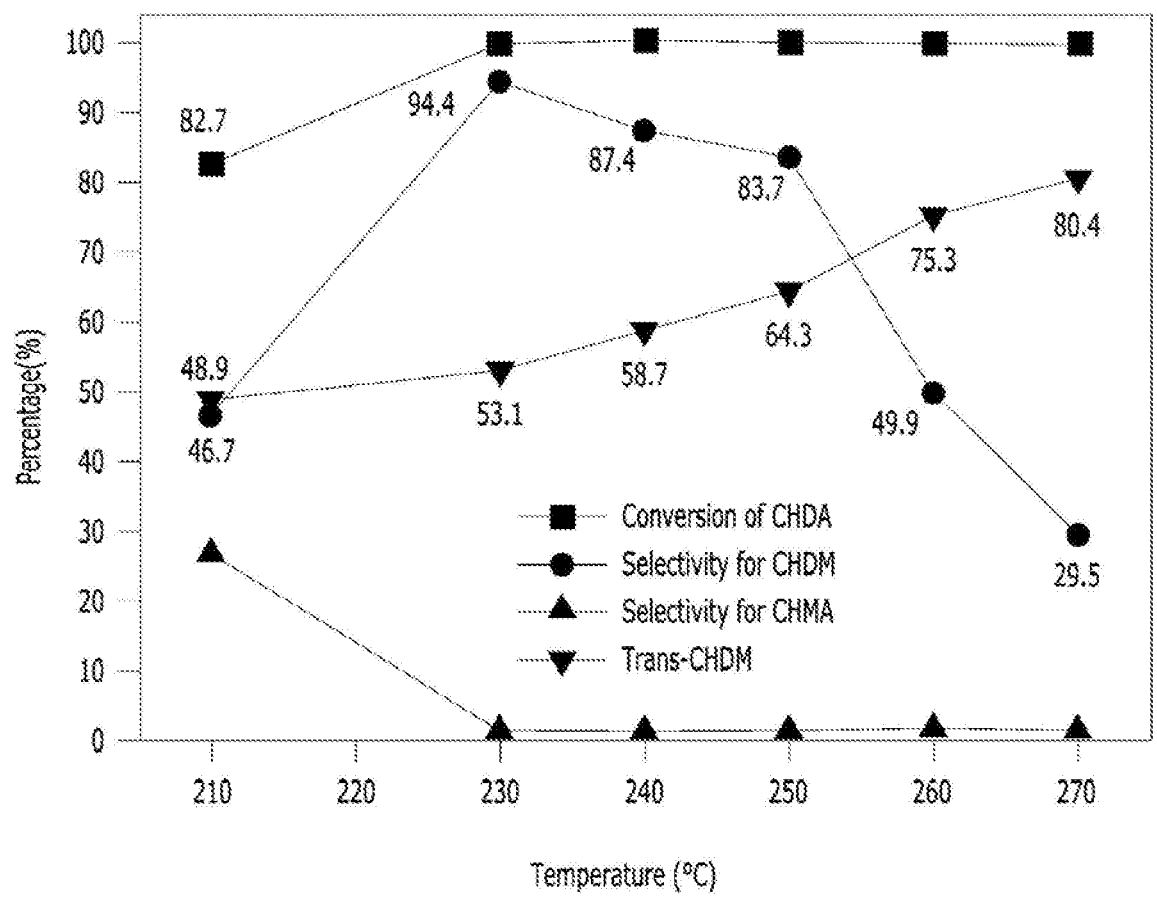
FIG. 1 is a CHDA hydrogenation reaction activity graph according to a reaction temperature in a process of preparing a cyclohexane dimethanol according to the present invention.

The present invention will be described with reference to specific embodiments and the accompanying drawings. The embodiments will be described in detail in such a manner that the present invention may be carried out by those of ordinary skill in the art. It should be understood that various embodiments of the present invention are different, but need not be mutually exclusive. For example, certain shapes, structures, and features described herein may be implemented in other embodiments without departing from the spirit and scope of the present invention in connection with one embodiment.

Therefore, the following detailed description is not to be taken in a limiting sense, and the scope of the present invention is to be limited only by the appended claims and the entire scope of equivalents thereof, if properly explained.

In addition, unless otherwise specified in the present specification, the term "substitution" or "substituted" means that one or more hydrogen atoms in the functional groups of the present invention are substituted with one or more substituents selected from the group consisting of a halogen atom (—F, —Cl, —Br, or —I), a hydroxy group, a nitro group, a cyano group, an amino group, an amidino group, a hydrazine group, a hydrazone group, a carboxyl group, an ester group, a ketone group, a substituted or unsubstituted alkyl group, a substituted or unsubstituted alicyclic organic group, a substituted or unsubstituted aryl group, a substituted or unsubstituted alkenyl group, a substituted or unsubstituted alkynyl group, a substituted or unsubstituted heteroaryl group, and a substituted or unsubstituted heterocyclic group. These substituents may be linked to each other to form a ring.

In the present invention, unless otherwise specified, the term "substituted" means that a hydrogen atom is substituted with a substituent such as a halogen atom, a $C_1$-$C_{20}$ hydrocarbon group, a $C_1$-$C_{20}$ alkoxy group, and a $C_6$-$C_{20}$ aryloxy group.

In addition, unless otherwise specified, the term "hydrocarbon group" refers to a linear, branched, or cyclic saturated or unsaturated hydrocarbon group. The alkyl group, the alkenyl group, the alkynyl group, and the like may be linear, branched, or cyclic.

In addition, unless otherwise specified in the present specification, the term "alkyl group" refers to a $C_1$-$C_{30}$ alkyl group and the term "aryl group" refers to a $C_6$-$C_{30}$ aryl group. In the present specification, the term "heterocyclic group" refers to a group in which one to three heteroatoms selected from the group consisting of O, S, N, P, Si, and any combination thereof are contained in one ring. Examples of the heterocyclic group may include pyridine, thiophene, and pyrazine, but the present invention is not limited thereto.

Hereinafter, embodiments of the present invention will be described with reference to the accompanying drawings, so that those of ordinary skill in the art can easily carry out the present invention.

As described above, the conventional cyclohexane dicarboxylic acid (CHDA) hydrogenation reaction technology has a limitation in the preparation of the cyclohexane dimethanol (CHDM) having a high trans content.

The present invention solves the above problems by providing a method for preparing a cyclohexane dimethanol (CHDM) by performing a hydrogenation reaction of a catalyst and a cyclohexane dicarboxylic acid (CHDA), wherein a weight ratio of the catalyst to the cyclohexane dicarboxylic acid (CHDA) is 1:1 to 1:5.

According to the present invention, the type of the catalyst is not particularly limited and may be preferably a ruthenium-based catalyst.

In general, a carrier on which ruthenium serving as an active ingredient is supported is a solid that disperses and stably retains a material having a catalytic function, and is usually a material having a large porosity or a large area so as to be highly dispersed and supported to increase the exposed surface area of the material having the catalytic function. The carrier has to be stable mechanically, thermally, and chemically. The type of the carrier is not limited.

The carrier may include any types of carriers that can be used as the carrier. Examples of the carrier may include silica, alumina, titanium oxide, zeolite, zinc oxide, starch, and synthetic polymer. Preferably, the carrier may be silica. However, the present invention is not limited thereto.

In addition, the hydrogenation catalyst may include a group 8 transition metal as the active ingredient. The hydrogenation catalyst may preferably include one or more selected from ruthenium (Ru), nickel (Ni), palladium (Pd), rhodium (Rh), platinum (Pt), and tin (Sn).

Specifically, according to the present invention, when the hydrogenation reaction is performed under a specific reaction condition, a cyclohexane dimethanol (CHDM) including at least one selected from a homogeneous additive and a heterogeneous additive may be prepared, or a cyclohexane dimethanol (CHDM) having a trans ratio of 60% to 95% may be prepared by adding a reactant having a trans content of a specific ratio. Preferably, a cyclohexane dimethanol (CHDM) having a trans ratio of 65% to 85% may be prepared.

First, according to the present invention, the specific reaction condition in the hydrogenation reaction may include a condition in which the hydrogenation reaction is performed in a temperature range of 200° C. to 280° C., a reaction pressure range of 50 bar to 150 bar, and a reaction time of 1 hour to 8 hours.

The type of the reactor in which such a hydrogenation reaction is performed is not particularly limited as long as the reactor can be used in the technical field to which the present invention pertains, and a batch reactor or a continuous reactor can be used. In addition, the reactor may include a heat control device that controls heat generated during the reaction.

In the present invention, the hydrogenation reaction may be performed within a temperature range of 200° C. to 280° C., preferably 210° C. to 270° C., and more preferably 230° C. to 250° C. In particular, when the reaction temperature is less than 200° C., the CHDA hydrogenation reaction may not be sufficiently activated, and thus, the selectivity and yield of the CHDM may be insufficient. When the reaction temperature exceeds 280° C., the yield of the CHDM may be reduced by side reaction. Therefore, the above range is preferable.

The hydrogenation reaction may be performed within a reaction pressure range of 50 bar to 150 bar, preferably 70 bar to 120 bar, and more preferably 90 bar to 120 bar. In particular, when the reaction pressure is less than 50 bar, hydrogen participating in the reaction may not be sufficiently present in a solvent, and thus, the activity may be deteriorated. When the reaction pressure exceeds 150 bar, a problem may occur in process stability. Therefore, the above range is preferable.

In addition, the hydrogenation reaction may be performed within a hydrogenation reaction time range of 1 hour to 8 hours, and preferably 1 hour to 6 hours. In particular, when the reaction time is less than 1 hour, the reaction may not be sufficiently performed, and thus, there may be a problem in obtaining the CHDM. When the reaction time exceeds 8 hours, the CHDM may be reduced by additional side reaction and a problem may occur in reaction efficiency.

In the hydrogenation reaction according to the present invention, the homogeneous additive and/or the heterogeneous additive may be included.

According to the present invention, the homogeneous additive is a material that is soluble in a solvent and may be at least one selected from the group consisting of ammonium bicarbonate ($NH_4HCO_3$), sodium hydroxide (NaOH), potassium carbonate ($K_2CO_3$), and sodium borohydride ($NaBH_4$). Preferably, the homogeneous additive may be ammonium bicarbonate ($NH_4HCO_3$).

When the homogeneous additive is ammonium bicarbonate ($NH_4HCO_3$), a weight ratio of the ammonium bicarbonate ($NH_4HCO_3$) to the catalyst may be 1:0.05 to 1:1. In particular, when the weight ratio of the ammonium bicarbonate to the catalyst is less than 1:0.05, it may be difficult to obtain a CHDM having a desired yield or selectivity. When the weight ratio of the ammonium bicarbonate to the catalyst exceeds 1:1, a reaction rate may be reduced. Therefore, the above range is preferable.

In addition, the heterogeneous additive is a material that is insoluble in a solvent and may include at least one metal oxide selected from the group consisting of zirconia, titania, ceria, silica, and magnesia. Preferably, the heterogeneous additive may be zirconia or titania.

When the heterogeneous additive is zirconia ($ZrO_2$), a weight ratio of the zirconia ($ZrO_2$) to the catalyst may be 1:0.5 to 1:3. In particular, when the weight ratio of the zirconia ($ZrO_2$) to the catalyst is less than 1:0.5, it may be difficult to obtain a cyclohexane dimethanol (CHDM) having a desired yield or selectivity. When the weight ratio of the zirconia ($ZrO_2$) to the catalyst exceeds 1:3, a reaction rate may be reduced. Therefore, the above range is preferable.

Finally, in the hydrogenation reaction according to the present invention, the reactants may be included in a single or mixed form.

According to the present invention, the reactant may be selected from cyclohexane dicarboxylic acids (CHDAs) having a cis form, a trans form, and a mixed form thereof. Preferably, the reactant may include a cyclohexane dicarboxylic acid (CHDA) having a high trans content.

In particular, the cyclohexane dicarboxylic acid (CHDA) may have a trans content of 5 to 99. Preferably, the trans content of the CHDA may be 50 to 99, and more preferably 60 to 95.

In some cases, the reactant may include a reactant obtained by isomerizing a cyclohexane dicarboxylic acid (CHDA) having a relatively low trans content.

MODE FOR CARRYING OUT THE INVENTION

Hereinafter, preferred examples are presented so as to help the understanding of the present invention. However, the following examples are for illustrative purposes only and the present invention is not limited by the following examples.

EXAMPLES

<Example 1> CHDA Hydrogenation Reaction Through Batch Reactor Type Catalytic Reactor A CHDA hydrogenation reaction was performed using a ruthenium-tin/alumina catalyst. For the CHDA hydrogenation reaction, a batch reactor capable of withstanding 300° C. and 150 bar was selected as the reactor. The reactor is an apparatus into which nitrogen for purging and hydrogen for hydrogenation reaction are introduced and which is capable of stirring for the reaction. As shown in Table 1 below, 4.05 g of a CHDA, 1.125 g of a catalyst, and 250 g of D.I. water, which were reactants, were added to a batch reactor. Purging was performed twice with nitrogen at 3 bar to 5 bar, and purging was performed twice with hydrogen at about 5 bar. While stirring (100 RPM) in a hydrogen atmosphere (about 15 bar), the batch reactor was heated to a reaction temperature of 270° C. When the reaction temperature was reached, hydrogen was injected to a reaction pressure of 100 bar, and then, the reaction was performed by increasing a stirring speed to 1,000 RPM.

During the CHDA hydrogenation reaction, a solution including the product and the reactants except for the solid-phase catalyst was sampled using a sampling port. The sampled liquid was analyzed using a gas chromatography apparatus equipped with a flame ionization detector (FID). The CHDA hydrogenation reaction was performed on the ruthenium-platinum-tin/alumina catalyst for 6 hours.

TABLE 1

|  | Catalyst (g) | CHDA(g) | Additive (g) |
|---|---|---|---|
| Example 1 | 1.125 | 4.05 | — |
| Example 2 | 1.125 | 4.05 | 0.4 ($NH_4HCO_3$) |
| Example 3 | 1.125 | 4.05 | 0.8 ($NH_4HCO_3$) |
| Example 4 | 1.125 | 4.05 | 0.4 ($ZrO_2$) |
| Example 5 | 1.125 | 4.05 | 0.4 ($TiO_2$) |
| Example 6 | 1.125 | 4.05 | 1.125 ($ZrO_2$) |
| Example 7 | 1.125 | 4.05 | 3.375 ($ZrO_2$) |

Examples 2 to 7

A CHDA hydrogenation reaction was performed in the same manner as in Example 1, except that an additive having a content shown in Table 1 was added.

EXPERIMENTAL EXAMPLES

1. CHDA Hydrogenation Reaction Activity According to Change in Reaction Temperature In the process of the CHDA hydrogenation reaction of Example 1, the reaction temperature was raised to 210° C. to 270° C. for 6 hours as a reaction condition, and the change in the CHDA reaction activity was measured. The results thereof are shown in FIG. 1 and Table 2 below.

TABLE 2

|  | Reaction temperature (° C.) | | | | | | |
|---|---|---|---|---|---|---|---|
|  | 210 | 220 | 230 | 240 | 250 | 260 | 270 |
| CHDM yield (%) | 46.7 | 65.7 | 94.4 | 87.4 | 83.7 | 49.9 | 29.5 |

As shown in FIG. 1 and Table 2, as the temperature was increased, the trans content was continuously increased. However, when the reaction temperature was about 230° C. or higher, the CHDM yield was reduced by side reaction. It was determined that this was caused by the accelerated thermal cracking reaction according to the increase in temperature (230° C. or higher).

2. CHDA Hydrogenation Reaction Activity According to Change in Reaction Time

After the CHDA hydrogenation reaction of Example 1 was performed, a solution (CHDM in D.I. water) produced through filtration was recovered. The reaction activity change and the CHDM trans ratio of the recovered reactant were measured with respect to the time change for 6 hours without catalyst in conditions of 250° C., 100 bar, and 1,000 RPM. The results thereof are shown in Table 3 below.

TABLE 3

| Reaction time (h) | 0 | 1 | 2 | 3 | 4 | 5 | 6 |
|---|---|---|---|---|---|---|---|
| Trans (%) | 60.8 | 61.0 | 61.2 | 61.5 | 61.8 | 62.1 | 62.5 |

As shown in Table 3, it was confirmed that the trans content was increased by about 2%.

3. CHDA Hydrogenation Reaction Activity According to Various Additives

Although the CHDA hydrogenation reaction of Example 1 was performed, $NH_4HCO_3$, $ZrO_2$, and $TiO_2$ were added as additives including the content ratios shown in Table 1. The reaction temperature was set to 250° C. for 3 hours as the reaction condition, and the change in the CHDA hydrogenation reaction activity was measured. The results thereof are shown in FIGS. 2 and 3.

Figure 2:
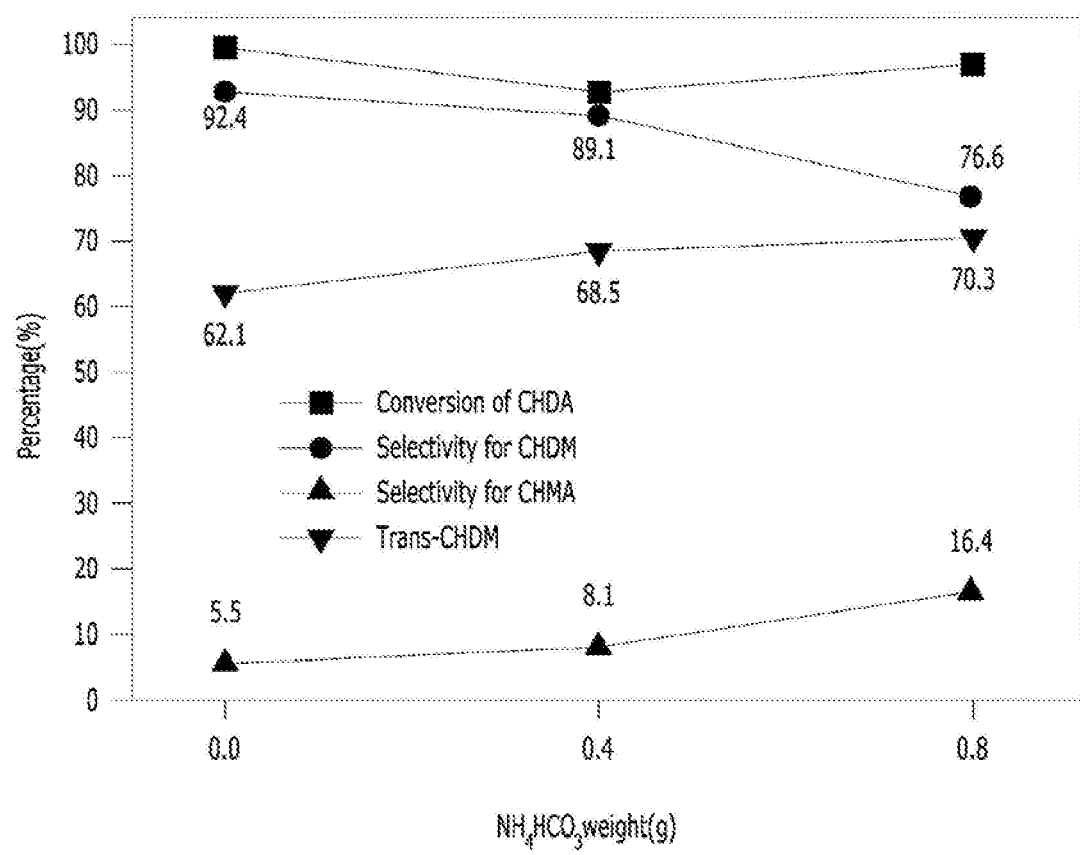
FIG. 2 is a CHDA hydrogenation reaction activity graph according to the introduction of $NH_4HCO_3$ in a process of preparing a cyclohexane dimethanol according to the present invention.
Figure 3:
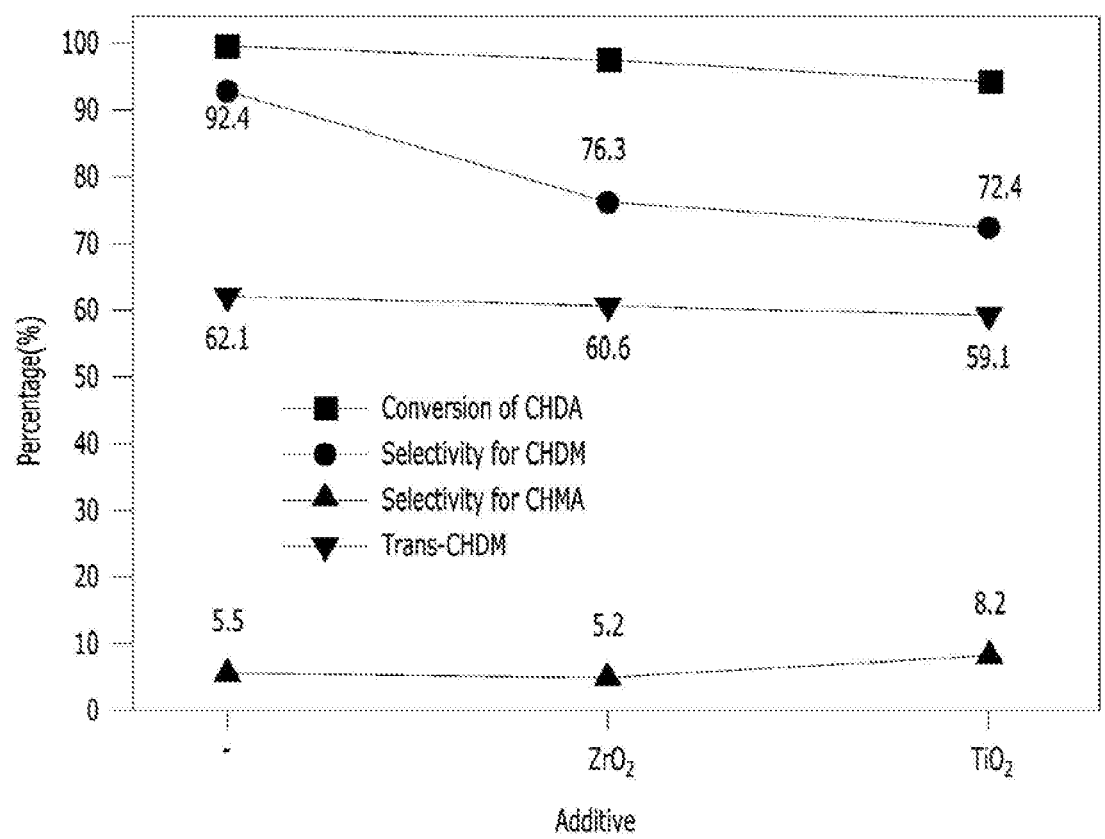
FIG. 3 is a CHDA hydrogenation reaction activity graph according to the introduction of zirconia and titania in a process of preparing a cyclohexane dimethanol according to the present invention.

As shown in FIGS. 2 and 3, when the additives including the content ratios as shown in Examples 2 to 5 were added, the CHDM selectivity and reaction rate were slightly decreased. In the case of Examples 2 and 3 in which $NH_4HCO_3$ was added as the additive, the trans content was increased. In the case of Examples 4 and 5 in which $ZrO_2$ or $TiO_2$ was added, the influence of the trans content was relatively small, as compared to Examples 2 and 3. Therefore, it can be seen that when the additives including the content ratios as shown in Examples 2 to 5 were added, it has a positive influence on the increase in the trans content of the CHDM.

4. CHDA Hydrogenation Reaction Activity with Excess of Zirconia Introduced as Additive The CHDA hydrogenation reaction of Example 1 was performed, but zirconia as the additive according to Table 1 was added in 1 to 3 times compared to the catalyst under the reaction condition of 230° C. for 6 hours. The conversion, selectivity, and trans content change results according to the CHDA hydrogenation reaction activity are shown in FIGS. 4 and 5.

Figure 4:
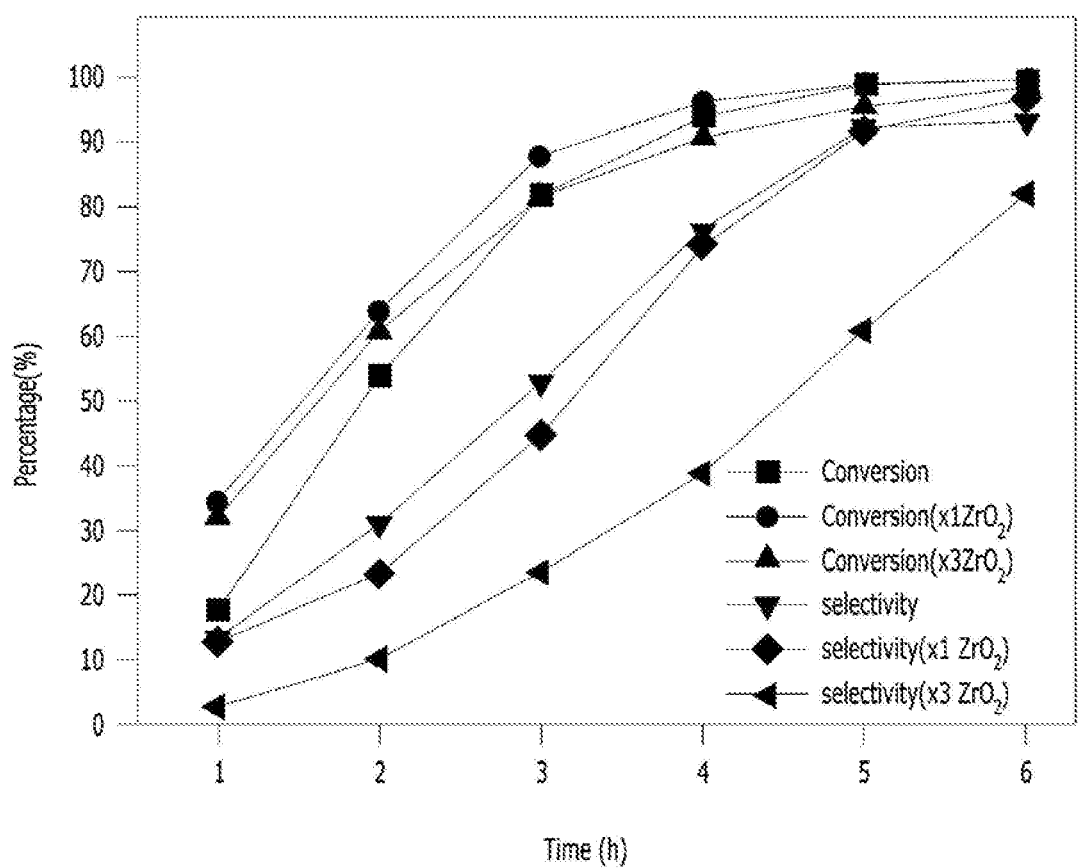
FIGS. 4 and 5 are graphs showing results of a CHDA hydrogenation reaction according to the introduction of zirconia in a process of preparing a cyclohexane dimethanol according to the present invention.
Figure 5:
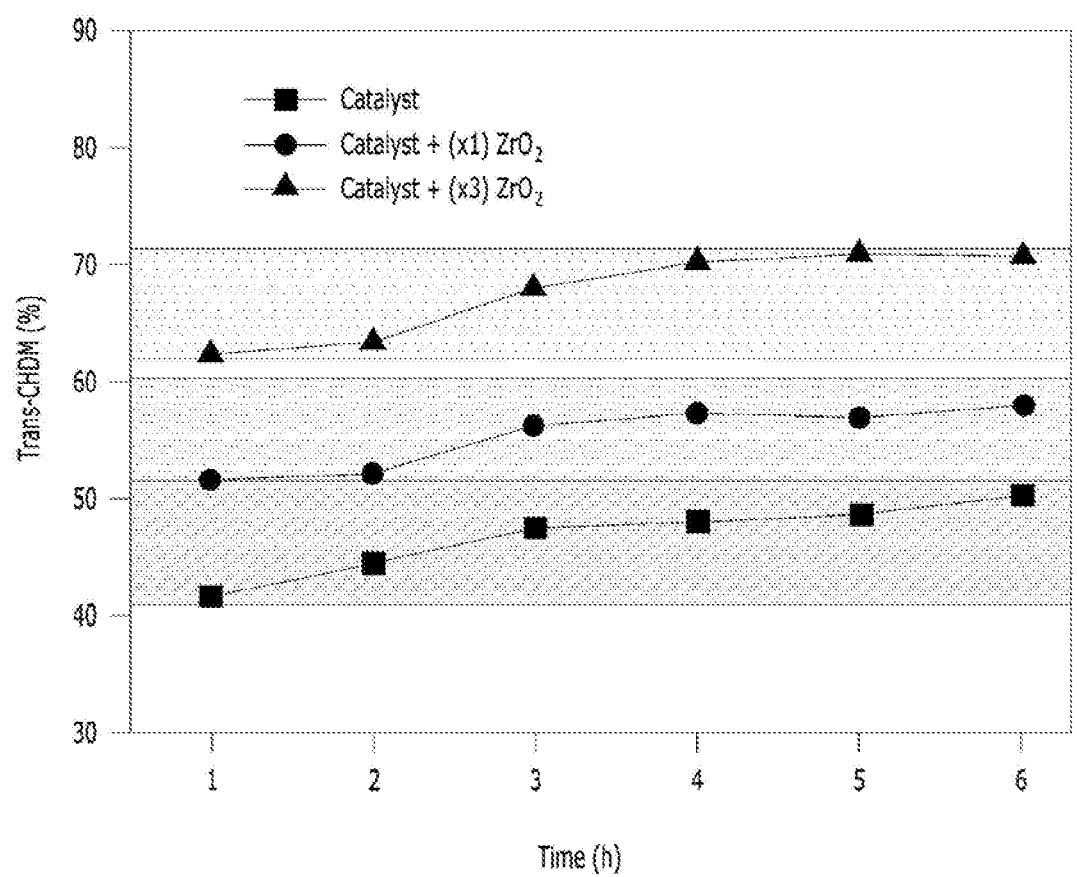

As shown in FIGS. 4 and 5, in the case of Example 6 in which zirconia was introduced 1 time compared to the amount of catalyst, a synergistic effect that the reaction activity was maintained and the trans content of the CHDM was increased was confirmed. In the case of Example 7 in which zirconia was introduced 3 times compared to the amount of the catalyst, the reaction rate was slightly decreased, but as a result, it was confirmed that the trans content of the CHDM was increased.

5. CHDA Hydrogenation Reaction Activity According to Type of Reactant

The CHDA hydrogenation reaction of Example 1 was performed, but the hydrogenation reaction experiment was performed using trans-CHDA 6.0% (cis-CHDA was purchased from TCI), trans-CHDA 10%, trans-CHDA 23.5% (CHDA was purchased from SK chemical), trans-CHDA 35%, trans-CHDA 50%, trans-CHDA 62.5% (isomerized after purchasing CHDA from SK chemical), and trans-CHDA 98.0% (trans-CHDA was purchased from TCI) as reactants. The results thereof are shown in Table 4 below and FIGS. 6 and 7.

TABLE 4

| Sample | 1 | 2 | 3 | 4 | 5 | 6 | 7 |
|---|---|---|---|---|---|---|---|
| Trans-CHDA (%) | 6 | 10 | 23.5 | 35 | 50 | 62.5 | 98.0 |
| CHDM trans (%) | 41.3 | 43.5 | 46.1 | 49.2 | 63.6 | 71.0 | 90.5 |

Figure 6:
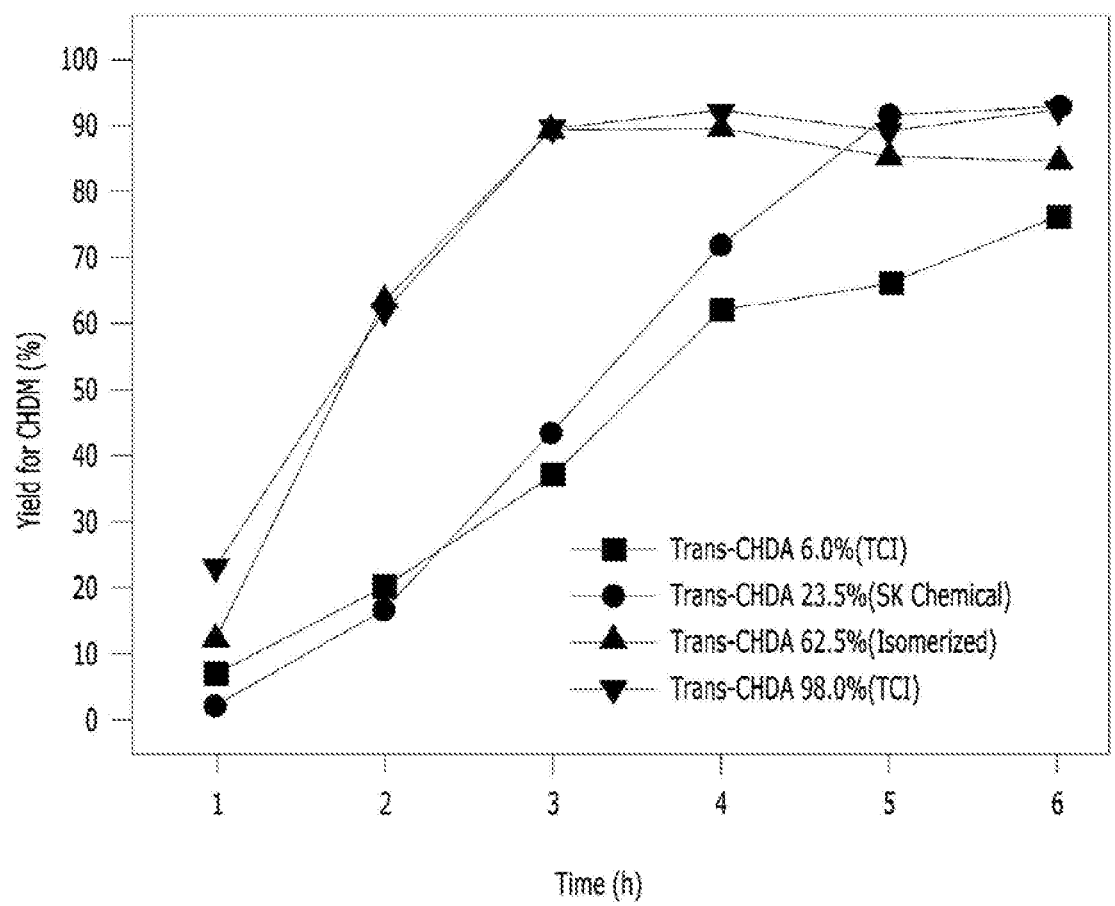
FIGS. 6 and 7 are graphs showing results of a hydrogenation reaction using a variety of trans content of CHDA in a process of preparing a cyclohexane dimethanol according to the present invention.
Figure 7:
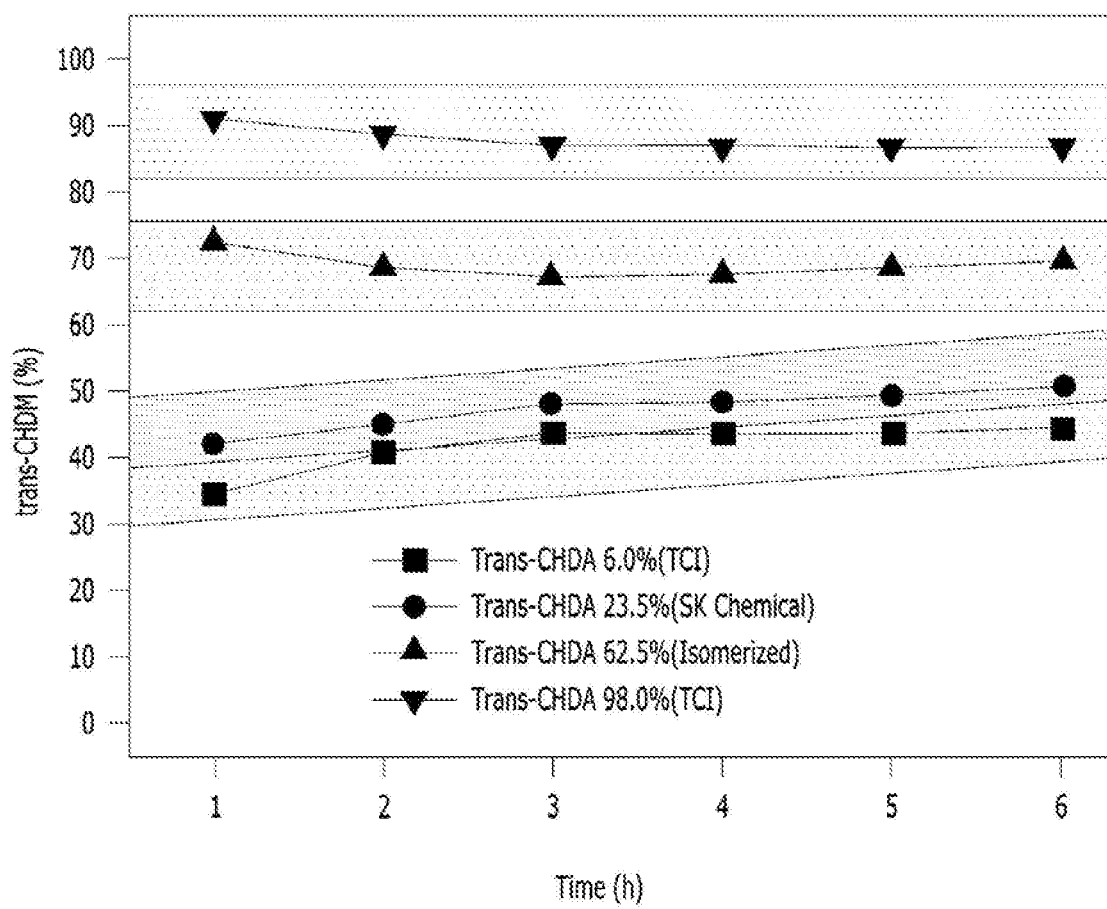

As shown in Table 4 and FIGS. 6 and 7, the case of the CHDA having a trans ratio of 50% or more (Samples 5 to 7) obtained the CHDM having a relatively high trans content, as compared to the case of the CHDA having a trans ratio of 6% to 35% (Samples 1 to 4). That is, it was confirmed that a CHDM having a high trans content could be obtained as a CHDA having a high trans content was used as a reactant.

Although the present invention has been described with reference to the drawings according to embodiments of the present invention, it will be understood by those of ordinary skill in the art that various applications and modifications can be made thereto without departing from the scope of the present invention.

The invention claimed is:

1. A method for preparing cyclohexane dimethanol (CHDM) by performing a hydrogenation reaction of cyclohexane dicarboxylic acid (CHDA) in the presence of a catalyst and at least one selected the group consisting of from a homogeneous additive and a heterogeneous additive,
    wherein a weight ratio of the catalyst to the cyclohexane dicarboxylic acid (CHDA) is 1:1 to 1:5,
    the catalyst is selected from the group consisting of ruthenium (Ru), palladium (Pd), rhodium (Rh), platinum (Pt), tin (Sn), and nickel (Ni),
    the homogeneous additive is selected from the group consisting of ammonium bicarbonate ($NH_4HCO_3$), sodium hydroxide (NaOH), potassium carbonate ($K_2CO_3$), and sodium borohydride ($NaBH_4$), and the heterogeneous additive is selected from the group consisting of zirconia, titania, ceria, and magnesia, wherein the heterogeneous additive is not carrier of the catalyst.

2. The method of claim 1, wherein a weight ratio of the homogeneous additive to the catalyst is 1:0.05 to 1:1.

3. The method of claim 1, wherein a weight ratio of the heterogeneous additive to the catalyst is 1:0.5 to 1:3.

4. The method of claim 1, wherein the hydrogenation reaction of the cyclohexane dicarboxylic acid (CHDA) is performed in a temperature range of 200° C. to 280° C.

5. The method of claim 1, wherein the hydrogenation reaction of the cyclohexane dicarboxylic acid (CHDA) is performed in a pressure range of 50 bar to 150 bar.

6. The method of claim 1, wherein the hydrogenation reaction of the cyclohexane dicarboxylic acid (CHDA) is performed for 1 hour to 8 hours.

7. The method of claim 1, wherein the cyclohexane dicarboxylic acid (CHDA) uses a reactant selected from a cis form, a trans form, and a mixed form thereof.

8. The method of claim 1, wherein the cyclohexane dimethanol (CHDM) has a yield of 85% to 99%.

9. The method of claim 1, wherein the catalyst includes at least one carrier selected from the group consisting of silica, alumina, titanium oxide, zeolite, zinc oxide, starch, and synthetic polymer.

10. The method of claim 1, wherein the method comprises an isomerization reaction process of the cyclohexane dicarboxylic acid (CHDA).

\* \* \* \* \*

UNITED STATES PATENT AND TRADEMARK OFFICE
CERTIFICATE OF CORRECTION

| | | |
|---|---|---|
| PATENT NO. | : 11,214,532 B2 | Page 1 of 1 |
| APPLICATION NO. | : 16/955421 | |
| DATED | : January 4, 2022 | |
| INVENTOR(S) | : Jong Kwon Lee et al. | |

It is certified that error appears in the above-identified patent and that said Letters Patent is hereby corrected as shown below:

In the Claims

Claim 1, Column 9, Line 19, after "selected", please insert --from--.

Claim 1, Column 9, Line 20, please delete "from".

Claim 1, Column 10, Line 2, after "ceria," please insert --silica--.

Signed and Sealed this
Twenty-fourth Day of January, 2023

Katherine Kelly Vidal
*Director of the United States Patent and Trademark Office*